US012788552B2

(12) United States Patent
Ellis

(10) Patent No.: US 12,788,552 B2
(45) Date of Patent: Nov. 10, 2026

(54) DISSOLVABLE STRETCH RING FOR INTRAOCULAR LENS

(71) Applicant: JelliSee Ophthalmics Inc., McLean, VA (US)

(72) Inventor: Forrest J. Ellis, McLean, VA (US)

(73) Assignee: JELLISEE OPHTHALMICS INC., McLean, VA (US)

( * ) Notice: Subject to any disclaimer, the term of this patent is extended or adjusted under 35 U.S.C. 154(b) by 426 days.

(21) Appl. No.: 18/386,857

(22) Filed: Nov. 3, 2023

(65) Prior Publication Data

US 2024/0148488 A1 May 9, 2024

Related U.S. Application Data

(60) Provisional application No. 63/422,538, filed on Nov. 4, 2022.

(51) Int. Cl.
*A61F 2/16* (2006.01)

(52) U.S. Cl.
CPC ........ *A61F 2/16* (2013.01); *A61F 2002/1682* (2015.04); *A61F 2002/16902* (2015.04);
(Continued)

(58) Field of Classification Search
CPC ............ A61F 2/1694; A61F 2002/1682; A61F 2002/16902; A61F 9/0026;
(Continued)

(56) References Cited

U.S. PATENT DOCUMENTS 6,413,277 B1 * 7/2002 Neuhann ............... A61F 2/1694 623/6.43
2005/0125058 A1 * 6/2005 Cumming ............. A61F 2/1613 623/6.37

(Continued)

FOREIGN PATENT DOCUMENTS

DE 20008676 U1 9/2000
DE 10308991 A1 9/2004

(Continued)

OTHER PUBLICATIONS

PCT Search Report and Written Opinion for corresponding Application Serial No. PCT/US2023/036785 mailed Jun. 2, 2024, pp. 1-26.

(Continued)

*Primary Examiner* — Javier G Blanco
(74) *Attorney, Agent, or Firm* — Tarolli, Sundheim, Covell & Tummino LLP

(57) ABSTRACT

A dissolvable stretch ring including a biodegradable polymer positioned on or adjacent to at least one haptic of an intraocular lens (IOL) is described. The dissolvable stretch ring can be included in an IOL arrangement, comprising an IOL an IOL body and at least one haptic extending directly or indirectly from the IOL body, and the dissolvable stretch ring. A method of implanting an IOL into an eye of a subject including the steps of inserting an IOL comprising an IOL body and at least one haptic extending directly or indirectly from the IOL body into the capsular bag of the eye and positioning a dissolvable stretch ring comprising a biodegradable polymer on at least one haptic of the IOL is also described.

11 Claims, 3 Drawing Sheets

(52) U.S. Cl.
CPC ................. *A61F 2210/0004* (2013.01); *A61F 2250/0031* (2013.01); *A61F 2250/0067* (2013.01)

(58) Field of Classification Search
CPC ...... A61F 2210/0004; A61F 2250/0031; A61F 2250/0067; A61F 2250/0068; A61F 2230/0065; A61K 9/0051; A61M 31/002; B29D 11/00096; A61L 27/54; A61L 27/58; A61L 31/16
See application file for complete search history.

(56) References Cited

U.S. PATENT DOCUMENTS

2013/0302398 A1* 11/2013 Ambati ................ A61K 9/2031 514/180
2015/0366660 A1* 12/2015 Fernández Martínez .................... A61F 2/16015 623/6.22
2016/0220351 A1* 8/2016 Dorronsoro Díaz .. A61F 2/1648
2018/0271646 A1* 9/2018 Marcos Celestino ........................ A61F 9/0079
2020/0022840 A1* 1/2020 Kahook ................ A61F 2/1613
2020/0405538 A1 12/2020 Mandell

FOREIGN PATENT DOCUMENTS

RU 2202987 C2 * 4/2003
WO WO-0030566 A1 * 6/2000 ............. A61F 2/161
WO 2003061625 A2 7/2003
WO 2009140246 A2 11/2009

OTHER PUBLICATIONS

Corresponding International Patent Application No. PCT/US2023/036785, International Preliminary Report on Patentability, date issued Apr. 29, 2025.

* cited by examiner

A

B

DISSOLVABLE STRETCH RING FOR INTRAOCULAR LENS

CROSS-REFERENCE TO RELATED APPLICATIONS

This application claims priority to U.S. Provisional Patent Application Ser. No. 63/422,538, filed Nov. 4, 2022, which is incorporated herein by reference.

BACKGROUND

Most cataract operations involve the implantation of an intraocular lens following cataract removal. Intraocular lenses (IOLs) have been developed and inserted into various locations of the eye and can be used to supplement or correct the vision provided by the natural crystalline lens of the eye or can replace the natural crystalline lens of the eye. Lenses that supplement or correct the vision without replacing the natural crystalline lens are typically referred to as Phakic Lenses while lenses that replace the natural crystalline lens are typically referred to as Aphakic or Pseudo-phakic lenses. Phakic lenses can be located within the anterior chamber (AC) of the eye (AC Phakic lenses) or the posterior chamber (PC) of the eye (PC Phakic Lenses). Typically, these lenses have a fixed focal length or, in the case of bifocal or multifocal lenses, have several different fixed focal lengths. Such fixed focal-length lenses lack the ability of the natural lens to dynamically change the refractive power of the eye.

A variety of new intraocular lens have been developed that provide an accommodating lens system which alters the refractive power of the eye in response to changes in tension of the ciliary muscle, thereby allowing the lens system to bring into focus images of objects that are both near and far from the eye.

Following cataract surgery involving implantation of an intraocular lens, it is necessary to administer pharmaceuticals to mitigate infection and control inflammation, ocular pressure, and other ocular conditions. With certain accommodating IOLs it is also desirable to administer pharmaceuticals that either relax the ciliary muscle to cause dis-accommodation or stimulate contraction of the ciliary muscle to cause accommodation. This maintains the eye in an accommodated or dis-accommodated state while the lens capsule contracts around the intraocular lens haptics, facilitating optimal function of the accommodating IOL. Accordingly, it would be preferable to provide a method of ocular surgery that did not rely on the patient to administer the pharmaceuticals via eye drops. In addition, intracameral placement of a sustained release pharmaceutical facilitates greater and sustained therapeutical levels of the pharmaceutical.

SUMMARY OF THE INVENTION

The present invention provides a non-permanent device that can dissolve and provide temporary support to either the IOL or to the lens capsule. In some embodiments, the device can also contain a sustained release agent.

In one aspect, the present invention provides a method of implanting an IOL into an eye of a subject. The method includes the steps of inserting an intraocular lens comprising an IOL body and at least one haptic extending directly or indirectly from the IOL body into the capsular bag of the eye, and positioning a dissolvable stretch ring comprising a biodegradable polymer on at least one haptic of the IOL. In some embodiments, the IOL is an accommodating IOL. In further embodiments, the method also includes the step of removing an existing lens from the eye of the subject while leaving the capsular bag of the eye intact.

In some embodiments, the IOL includes a plurality of haptics. In some embodiments, the dissolvable stretch ring includes a plurality of positioning tabs configured to fit between the haptics of the IOL. In further embodiments, the dissolvable stretch ring comprises a hyaluronic acid derivative. In yet further embodiments, the subject has been diagnosed as having one or more cataracts.

In an additional embodiment, the dissolvable stretch ring is positioned on or adjacent to the at least one haptic of the IOL by delivering the dissolvable stretch ring using an implantation device comprise a sleeve for holding the dissolvable stretch ring and a push rod positioned within the sleeve, wherein applying pressure to the push rod pushes the dissolvable stretch ring out of the implantation device and onto the at least one haptic of the IOL.

Another aspect of the present invention provides an intraocular lens (IOL) arrangement. The IOL arrangement includes an IOL comprising an IOL body and at least one haptic extending directly or indirectly from the IOL body and a dissolvable stretch ring comprising a biodegradable polymer positioned on at least one haptic of the IOL. In some embodiments, the IOL is an accommodating IOL. In further embodiments, the IOL includes a plurality of haptics. In yet further embodiments, the dissolvable stretch ring includes a plurality of positioning tabs configured to fit between the haptics of the IOL. In some embodiments, the dissolvable stretch ring comprises a hyaluronic acid derivative. In further embodiments, the dissolvable stretch ring comprises an ophthalmological drug.

DETAILED DESCRIPTION OF THE INVENTION

Figure 1A:
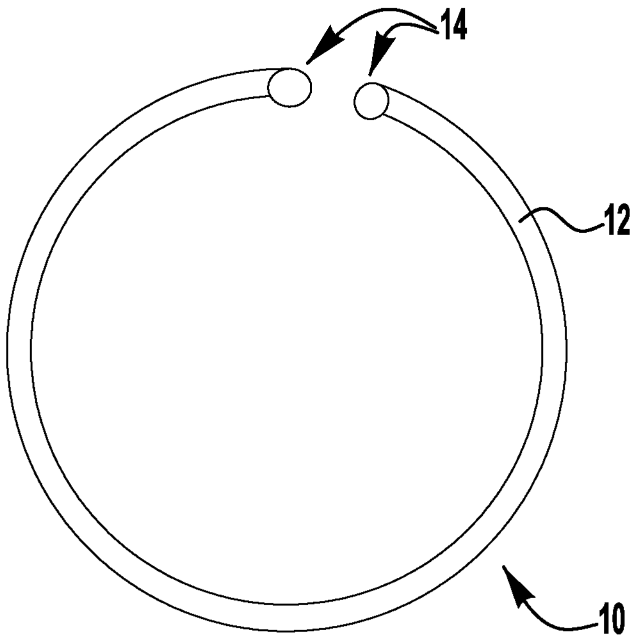
FIGS. 1A and 1B provide a representation of A) a dissolvable stretch ring and b) the dissolvable stretch ring positioned over the haptics of an intraocular lens.

The present invention provides a dissolvable stretch ring including a biodegradable polymer positioned on at least one haptic of the intraocular lens. The dissolvable stretch ring can be included in an intraocular lens arrangement, comprising an intraocular lens comprising an IOL body and at least one haptic extending directly or indirectly from the IOL body, and the dissolvable stretch ring. The invention also provides a method of implanting an IOL into an eye of a subject including the steps of inserting an IOL comprising at least one haptic into the capsular bag of the eye and positioning a dissolvable stretch ring comprising a biodegradable polymer on at least one haptic of the IOL.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "comprises," "comprising," "includes," "including," "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The conjunctive phrase "and/or" indicates that either or both of the items referred to can be present.

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts at toxic concentrations, does not cause prolonged inflammation or irritation, or does not induce more than a basal immune reaction in the host.

The term "biodegradable" as used herein refers to a biocompatible polymer that can be broken down by either chemical or physical process, upon interaction with the physiological environment subsequent to use, and erodes or dissolves within a period of time, typically within days, weeks or months. A biodegradable material serves a temporary function in the body, such as imaging a tissue region, and is then degraded or broken into components that are metabolizable or excretable.

As used herein, "treatment" means any manner in which the symptoms of a defect, condition, disorder, or disease, or any other indication, are ameliorated or otherwise beneficially altered.

Dissolvable Stretch Ring

In one aspect, the present invention provides a dissolvable stretch ring comprising a biodegradable polymer. The ring is dissolvable in that it is biodegradable, such that the ring will break down and degrade over time rather than remaining permanently positioned over an intraocular lens (IOL) when placed in the aqueous environment of the eye. In addition, the ring has sufficient elasticity to allow it to be stretched to fit over the haptics of the IOL. The dissolvable stretch ring may be any suitable form, such as a ring, a partial ring or ring segment, multiple ring segments, or a polygon.

The dissolvable stretch ring will break down and degrade after being implanted in the eye. This provides the advantage of not requiring surgical removal of the stretch ring after it is no longer necessary, while also allowing an accommodating IOL to resume its normal ability to move between accommodating and dis-accommodating states once the dissolvable stretch ring has degraded and is no longer applying pressure. Preferably the dissolvable stretch ring degrades at a rate such that it has degraded by 90% or more within a time ranging from about two weeks to about two months, while in some embodiments it will degrade by 90% or more within about a month.

Examples of biodegradable polymers include polylactide polymers include poly(D,L-Lactide)s; poly(lactide-co-glycolide) (PLGA) copolymers; polyglycolide (PGA) and polydioxanone; caprolactone polymers; chitosan; carboxymethyl cellulose, ethyl cellulose, cellulose acetate; poly (butylene succinate), poly(vinyl alcohol), poly(hydroxybutyrate); polyanhydrides and polyesters; hyaluronic acid, and hyaluronic acid derivatives.

In some embodiments, the dissolvable stretch ring comprises a hyaluronic acid derivative. Hyaluronic acid derivatives are hyaluronic acid polymers that have been modified to include an additional chemical group. Examples of hyaluronic acid derivatives include hyaluronic acid alkyl derivatives. An example of a specific hyaluronic acid derivative is methacrylated hyaluronic acid.

FIG. 1A provides an image of a dissolvable stretch ring. The dissolvable stretch ring 10 includes an open ring 12 made of a biodegradable polymer, and an eyelet 14 at each end of the open ring. The dissolvable stretch ring may be circular in its resting state, or it may simply be capable of forming a circle or partial circle when placed upon the haptics of an intraocular lens.

Figure 2A:
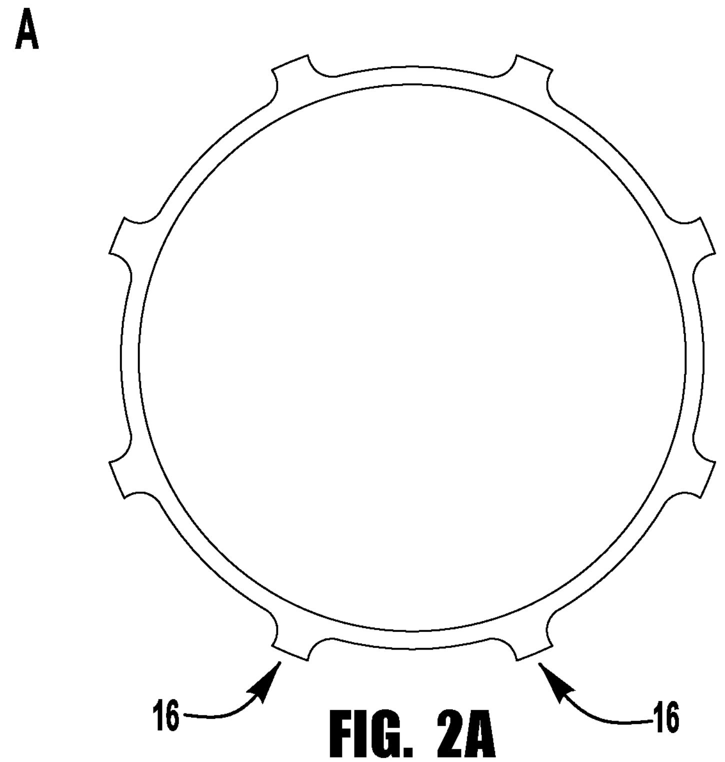
FIGS. 2A and 2B provide a representation of A) a dissolvable stretch ring including positioning tabs and B) the dissolvable stretch ring including positioning tabs positioned on a multi-arm intraocular lens.

A further embodiment of the dissolvable stretch ring is shown in FIG. 2A. In this embodiment, the dissolvable stretch ring 10 includes a plurality of positioning tabs 16 configured to fit between the haptics of an IOL. In many embodiments, the positioning tabs 16 are positioned at regular intervals around the circumference of the dissolvable stretch ring. The dissolvable stretch ring can include a number of positioning tabs equal to the number of haptics present on the IOL that you intend to fit it to. For example, when configured to fit between the haptics of an intraocular lens having eight haptics, the dissolvable stretch ring can include eight positioning tabs. However, in some embodiments, the number of positioning tabs may be less than the number of haptics present on the IOL.

In some embodiments, the dissolvable stretch ring is attached to the posterior recess of the haptics. This may be placed during manufacturing or prior to insertion of the accommodating IOL into the eye, or after insertion into the eye. For example, the drug-delivering ring can form a stabilizing ring to keep the haptics from holding inwards with lens capsule fibrosis. See for example the stabilizing ring described in WO 2022/016130, the disclosure of which is incorporated herein by reference.

The dimensions of the drug-delivering stretch ring should be selected to facilitate placement on or in the eye or an intraocular lens. Preferably the drug-delivering stretch ring has a diameter from about 5 mm to about 15 mm, or in some embodiments from about 10 to about 15 mm. A diameter of about 11 to about 13.5 mm is preferred for placement on the periphery of the capsular bag adjacent to the IOL, while a diameter of about 9.5 mm to about 10.5 mm is preferred to placement on the haptics of an accommodating IOL. The width or thickness of the ring is typically 2 mm or less (e.g., from about 0.2 mm to about 1.5 mm).

In some embodiments, the dissolvable stretch ring includes at least one medication. For example, the medication can be selected from the group comprising anti-fibrotic agent, anti-inflammatory agent, immunosuppressant agent, anti-neoplastic agent, migration inhibitors, anti-proliferative agent, intraocular pressure lowering agents, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelia, matrix metalloproteinase inhibitors, CNPA, corticosteroids, cenegermin, cyclosporine, cysteamine hydrochloride, mitomycin, sodium chloride hypertonic, netarsudil, and riboflavin 5' phosphate and/or antibody-based immunosuppressants.

Lens Arrangement

An additional aspect of the invention provides an intraocular lens (IOL) arrangement. The IOL arrangement includes an IOL comprising an IOL body and at least one haptic extending directly or indirectly from the IOL body; and a dissolvable stretch ring comprising a biodegradable polymer positioned (e.g., non-permanently attached) on at least one haptic of the IOL. In some embodiments, the intraocular lens is an accommodating intraocular lens. In some embodiments, the IOL includes a plurality of haptics.

Figure 1B:
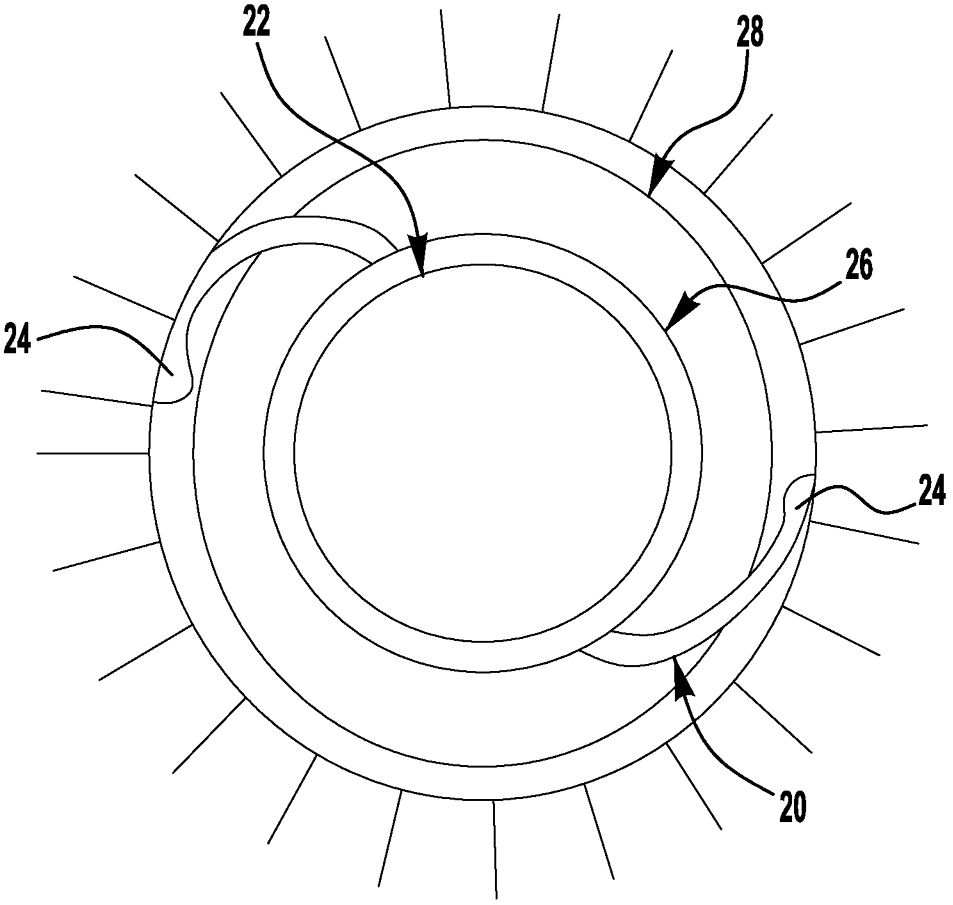

FIG. 1B shows an intraocular lens arrangement. The intraocular lens 20 has been positioned over the anterior opening 22 in the lens capsular bag. The intraocular lens 20 includes a pair of haptics 24 that extend from the body 26 of the intraocular lens 20 to the peripheral lens capsular bag 28. The arrangement also includes a dissolvable stretch ring 10 positioned over or adjacent to the haptics 24 and along the edge of the peripheral capsular bag 28.

Figure 2B:
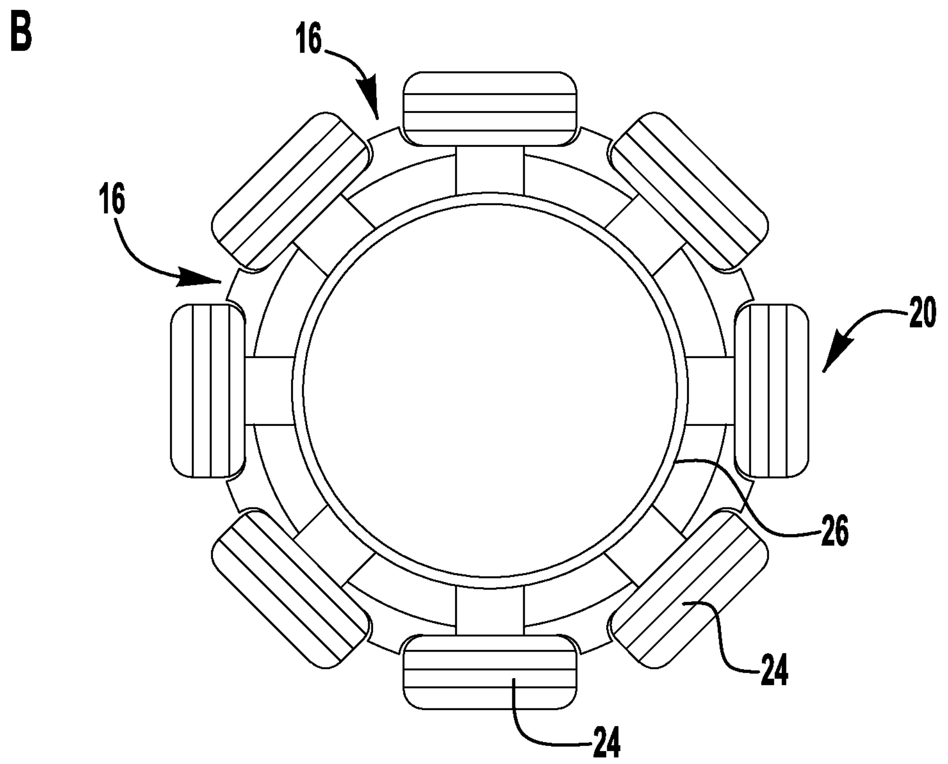

FIG. 2B shows an intraocular lens arrangement including a dissolvable stretch ring comprising a plurality of positioning tabs 16. In this embodiment, the intraocular lens 20 includes a plurality of haptics 24 positioned around the body 26 of the intraocular lens 20. The positioning tabs 16 are positioned between the haptics 24 of the intraocular lens. In some embodiments, the dissolvable stretch ring 10 includes a plurality of positioning tabs 16 configured to fit between the haptics 24 of the intraocular lens 20.

In some embodiments, the present invention relates to an arrangement of the dissolvable stretch ring with ophthalmic devices including IOLs and more particularly to accommodating IOLs. In a further embodiment, an IOL can comprise a shape-changing optic. The IOL can be configured to assume an accommodated state, a dis-accommodated state, and states therebetween.

In some embodiments, the IOL can comprise an elastic anterior face located anterior to the equator, having an anterior surface and a posterior surface, and having a periphery. The IOL can also include a posterior face having an anterior surface, a posterior surface, and a periphery. The IOL can further include an elastic side wall extending across the equator and extending from the anterior face to the posterior face. The IOL additionally can include a chamber containing material that is located between the anterior face and the posterior face. The IOL can also include at least one haptic having a medial portion and a lateral portion. The medial portion can extend (directly or indirectly) from the periphery of the anterior face, the periphery of the posterior face, or both. In certain aspects, the at least one haptic comprises a plurality of haptics, each having a medial portion and a lateral portion, the medial portion extending from and connected to the periphery of the anterior face such that the plurality of haptics changes the shape of the anterior face via tensile or compressive forces. The anterior face can be more resistant to deformational change than the material contained within the chamber. See U.S. Pat. No. 11,357,618, the disclosure of which is incorporated herein by reference.

In another aspect an IOL has an optical axis extending in an anterior-posterior direction and an equator extending in a plane substantially perpendicular to the optical axis. The IOL can comprise an elastic anterior face located anterior to the equator, and a posterior face located posterior to the equator. The anterior face, the posterior face, or both can comprise a poly(dimethylsiloxane) elastomer having a durometer between about 30 Shore A to about 50 Shore A. A chamber can be located between the anterior face and the posterior face and can comprise a silicone oil comprising polysiloxanes comprising diphenyl siloxane and dimethyl siloxane units. The silicone oil has a maximum viscosity of about 700 $mm^2/s$ at 25° C. and has a mean molecular weight of less than about 3000 Daltons.

In another aspect, an IOL has an optical axis extending in an anterior-posterior direction and an equator extending in a plane substantially perpendicular to the optical axis. The IOL can comprise an elastic anterior face located anterior to the equator and a posterior face located posterior to the equator. The anterior face, the posterior face, or both can comprise a polysiloxane that is at least 99% poly(dimethylsiloxane) elastomer. The IOL can further include a chamber located between the anterior face and the posterior face and can comprise a silicone oil comprising polysiloxanes comprising diphenyl siloxane and dimethyl siloxane units.

Method of Implanting an Intraocular Lens

Another aspect of the invention provides a method of implanting an intraocular lens (IOL) into an eye of a subject. The method includes the steps of inserting an IOL comprising an IOL body and at least one haptic extending directly or indirectly from the IOL body into the capsular bag of the eye and positioning a dissolvable stretch ring comprising a biodegradable polymer on at least one haptic of the IOL. Alternately, in other embodiments, the dissolvable stretch ring can be positioned on the IOL before insertion into the eye. During cataract surgery, the lens anterior capsule and entire fiber mass are removed, and an artificial intraocular lens (IOL) is inserted into the eye chamber with posterior capsule still intact. Accordingly, in some embodiments, the method further comprises the step of removing an existing lens from the eye of the subject while leaving the capsular bag of the eye intact. The dissolvable stretch ring can be placed on the IOL either before or after the IOL has been implanted in the eye.

In some embodiments, the IOL is an accommodating IOL. In further embodiments, the IOL includes a plurality of haptics. In yet further embodiments, the dissolvable stretch ring includes a plurality of positioning tabs configured to fit between the haptics of the IOL.

Figure 3A:
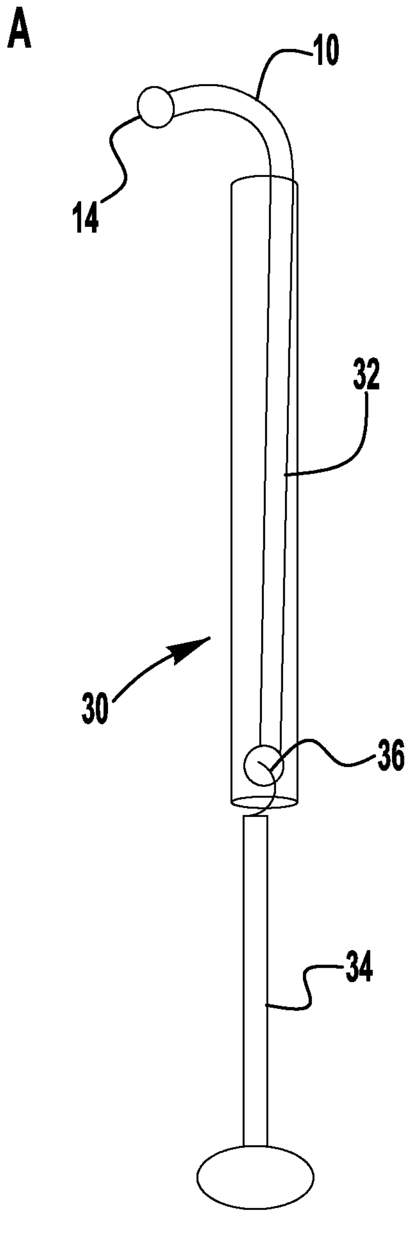
FIGS. 3A and 3B provide a representation of an implantation device for a dissolvable stretch ring, with A) showing the dissolvable stretch ring within the implantation device before use, and B) showing the extruded dissolvable stretch ring after pressure had been applied to a push rod of the implantation device.
Figure 3B:
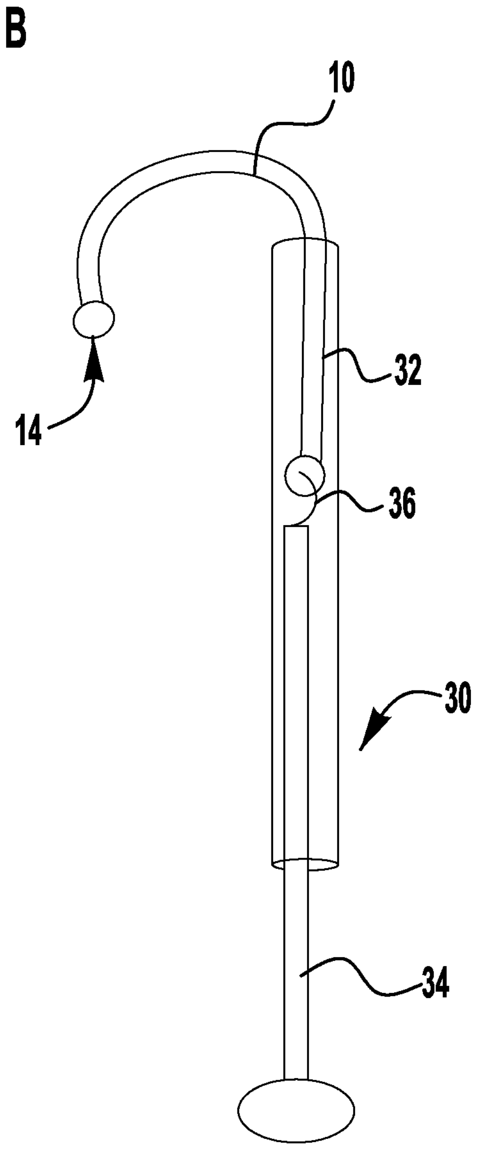

The dissolvable stretch ring can be positioned on the intraocular lens using an implantation device. An implantation device 30 suitable for use with a dissolvable stretch ring is shown in FIG. 3. The implantation device 30 include a sleeve 32 in which the dissolvable stretch ring 10 is held, and a push rod 34 that fits within the sleeve 32. FIG. 3A shows the dissolvable stretch ring within the implantation device before use, while FIG. 3B shows the extruded dissolvable stretch ring 10 after pressure had been applied to a push rod 34 of the implantation device 30. In some embodiments, the pressure rod 34 includes a hook 36 that can fit into an eyelet 14 of the dissolvable stretch ring 10 to facilitate handling of the dissolvable stretch ring 10.

Accordingly, in some embodiments the dissolvable stretch ring is positioned on at least one haptic of the IOL by delivering the dissolvable stretch ring using an implantation device comprise a sleeve for holding the dissolvable stretch ring and a push rod positioned within the sleeve, wherein applying pressure to the push rod pushes the dissolvable stretch ring out of the implantation device and onto at least one haptic of the IOL.

One benefit of using a partial ring or ring segment as the dissolvable stretch ring, rather than a full ring, is that the partial ring can be more easily manipulated both when installing and removing the dissolvable stretch ring. More particularly, the partial ring can be wrapped into place on the haptics, rather than having to be stretched or compressed over the haptics as may be required with a full ring. Also, when using a partial ring or ring segment as the dissolvable stretch ring, rather than a full ring, the partial ring can be detached from the haptics by grasping one free end and directing the ring away from the haptics, essentially unwinding the device to free the device from the haptics without the need to stretch or compress the device in order to displace it.

When implanting an accommodating IOL, it is preferable to dis-accommodate the IOL. This maintains the eye in a dis-accommodated state while the lens capsule contracts around the intraocular lens haptics, facilitating optimal function of the accommodating IOL. Typically this is done by relaxing the ciliary muscle. However, dis-accommodation of the IOL can also be achieved by providing outward force from a dissolvable stretch ring of the present invention that has been positioned on the IOL. The dissolvable stretch ring can provide an outward force of from about 0.2 to about 0.12 newtons. In some embodiments, an outward force (i.e., compression resistance) of about 0.5 to about 0.9 newtons is provided, while in further embodiments an outward force of about 0.6 to about 0.8 newtons is provided. The outward pressure can be provided by using a C-shaped (i.e., partial ring) dissolvable stretch ring. As the dissolvable stretch ring dissolves, the outward force is gradually reduced until the IOL is again able to move to the accommodating state and the accommodating IOL is able to function normally. Preferably the accommodating IOL is maintained in the dis-accommodated state for about a month after implantation.

In some embodiments, the subject has been diagnosed as having one or more cataracts. A cataract is a clouding or development of an opaque area in the lens. Most cataracts form as part of the aging process, but some are associated with congenital or systemic pathological conditions and others are related to ocular trauma. Cataracts are formed by the clumping of the proteins in the lens and the opacification that ensues, which hinders light transmission and normal vision. In cataract surgery, the lens anterior capsule and fiber mass are removed, and an artificial intraocular lens is inserted into the eye chamber with the posterior capsule still intact.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of implanting an intraocular lens (IOL) into an eye of a subject, comprising:
- inserting an accommodating IOL comprising an IOL body and at least one haptic extending directly or indirectly from the IOL body into the capsular bag of the eye, and
- positioning a dissolvable stretch ring comprising a biodegradable polymer on at least one haptic of the IOL,
- wherein the biodegradable polymer comprises a hyaluronic acid derivative,
- wherein the dissolvable stretch ring is sized and configured to be positioned along the edge of a peripheral capsular bag, and
- wherein the dissolvable stretch ring provides an outward force of about 0.6 newtons to about 0.8 newtons.

2. The method of claim 1, further comprising the step of removing an existing lens from the eye of the subject while leaving the capsular bag of the eye intact.

3. The method of claim 1, wherein the IOL includes a plurality of haptics.

4. The method of claim 3, wherein the dissolvable stretch ring includes a plurality of positioning tabs configured to fit between the haptics of the IOL.

5. The method of claim 1, wherein the dissolvable stretch ring degrades by 90% or more within about a month after implantation.

6. The method of claim 1, wherein the dissolvable stretch ring is positioned on the at least one haptic of the IOL by delivering the dissolvable stretch ring using an implantation device comprise a sleeve for holding the dissolvable stretch ring and a push rod positioned within the sleeve, wherein applying pressure to the push rod pushes the dissolvable stretch ring out of the implantation device and onto the at least one haptic of the IOL.

7. The method of claim 1, wherein the subject has been diagnosed as having one or more cataracts.

8. An intraocular lens (IOL) arrangement, comprising:
- an accommodating IOL comprising an IOL body at least one haptic extending directly or indirectly from the IOL body; and
- a dissolvable stretch ring comprising a biodegradable polymer positioned on at least one haptic of the IOL,
- wherein the biodegradable polymer comprises a hyaluronic acid derivative,
- wherein the dissolvable stretch ring is sized and configured to be positioned along the edge of a peripheral capsular bag, and
- wherein the dissolvable stretch ring provides an outward force of about 0.6 newtons to about 0.8 newtons.

9. The IOL arrangement of claim 8, wherein the IOL includes a plurality of haptics.

10. The IOL arrangement of claim 8, wherein the dissolvable stretch ring includes a plurality of positioning tabs configured to fit between the at least one haptic of the IOL.

11. The IOL arrangement of claim 8, wherein the dissolvable stretch ring comprises an ophthalmological drug.

* * * * *